United States Patent [19]

Seagraves

[11] 4,212,824
[45] Jul. 15, 1980

[54] HYDROGENATION CATALYST WITH IMPROVED METALLIC DISTRIBUTION, ITS PREPARATION AND USE FOR THE REDUCTION OF AROMATIC NITRO COMPOUNDS

[75] Inventor: Robert L. Seagraves, Pennsville, N.J.

[73] Assignee: E. I. Du Pont de Nemours and Company, Wilmington, Del.

[21] Appl. No.: 923,568

[22] Filed: Jul. 11, 1978

[51] Int. Cl.$^2$ .................. C07C 85/11; B01J 21/18; B01J 23/42; B01J 23/74
[52] U.S. Cl. ............................... 260/580; 252/447
[58] Field of Search ................. 252/447, 472; 260/580

[56] References Cited
U.S. PATENT DOCUMENTS

| | | | |
|---|---|---|---|
| 2,823,235 | 2/1958 | Graham | 260/580 |
| 3,499,034 | 3/1970 | Gonzalez | 260/580 |

*Primary Examiner*—W. J. Shine

[57] ABSTRACT

An iron-modified, platinum hydrogenation catalyst useful for the reduction of aromatic nitro compounds is provided. The catalyst, having improved distribution of the metallic components on an oleophilic carbon support as shown by ESCA analysis, is prepared by depositing a platinum compound (oxide, hydroxide or carbonate) on the carbon support at a temperature in the range of 55°–95° C., preferably 90°–95° C., and then reducing the compound to platinum metal, preferably with formaldehyde, at a temperature less than about 35° C. The iron in the catalyst is present and deposited as its oxide or hydroxide either at the same temperature as the platinum compound or at a temperature less than about 35° C. Using such a catalyst to reduce halogen-substituted nitro aromatic compounds to the corresponding amines results in low dehalogenation, low tar formation and hydroxylamine accumulation. For nonhalogenated nitro aromatic reductions, the catalyst minimizes ring reduction.

17 Claims, No Drawings

HYDROGENATION CATALYST WITH IMPROVED METALLIC DISTRIBUTION, ITS PREPARATION AND USE FOR THE REDUCTION OF AROMATIC NITRO COMPOUNDS

DESCRIPTION

1. Technical Field

This invention relates to hydrogenation catalysts, their preparation and use in the hydrogenation of aromatic nitro compounds and more particularly to platinum/iron hydrogenation catalysts particularly useful for the hydrogenation of chloronitro aromatic compounds.

2. Background Art

The hydrogenation of aromatic nitro compounds, including chloro-substituted derivatives, to corresponding amines by the formation of corresponding nitroso compounds and hydroxylamines as intermediates is well known in the art. These intermediates will condense with the amine products and with themselves to form azoxy, azo and hydrazo derivatives which can form tar-like substances. As a result, yields are lowered and the quality of the final product is reduced. Furthermore, hydroxylamines disproportionate exothermically and any buildup in their concentration in a reaction system is potentially hazardous. The hydrogenation of chloro-substituted derivatives poses another problem because of dechlorination reactions which occur during the process.

The art has attempted to solve the aforesaid dechlorination, tar and low yield problems for many years. Illustrative attempted solutions are the use of different catalysts (e.g., U.S. Pat. No. 2,823,235, issued Feb. 11, 1958 to Graham et al.) or of different processing techniques for the hydrogenation (e.g., U.S. Pat. No. 3,499,034, issued Mar. 3, 1970 to Gonzalez). It still remains that these problems are not eliminated, especially depending upon the amine made and whether the process used is a batch process.

DISCLOSURE OF THE INVENTION

According to the present invention, there is provided a hydrogenation catalyst consisting essentially of an oleophilic carbon black support having a surface area below about 300 $m^2/g$, said support having on its surface about 0.1–10 percent by weight of the support of platinum metal, and iron in the form of its oxide, hydroxide or carbonate, the molar ratio of iron to platinum being in the range of about 2:1–16:1, said catalyst having:

(1) a ratio of platinum/carbon ESCA (infra) intensity ratio to the total platinum content, expressed by its weight percent concentration/100, of at least about 2.4; and (2) a ratio of the iron/carbon ESCA (infra) intensity ratio to the platinum/carbon ESCA (infra) intensity ratio of at least about 0.6.

There is also provided a process for improving the distribution of metallic component in the preparation of a hydrogenation catalyst having a carbon black support comprising: (a) depositing onto oleophilic carbon black particles having a surface area less than about 300 $m^2/g$, at a temperature in the range of about 55°–95° C., an oxide, hydroxide or carbonate of platinum, the concentration of the platinum being in the range of about 0.1–10 percent by weight based on the weight of the carbon black; (b) depositing an oxide, hydroxide or carbonate of iron onto the carbon black particles in an amount to provide a molar ratio of iron to platinum in the range of about 1:1–16:1; and (c) reducing the platinum oxide, hydroxide or carbonate to platinum metal at a temperature less than about 35° C.

Further provided is an improved process for preparing an aromatic amine by hydrogenating the corresponding nitro compound in the presence of a noble metal catalyst wherein the improvement comprises hydrogenating the nitro compound in the presence of the aforesaid catalyst.

The present invention is based on the discovery that the platinum and iron distribution on a nonporous carbon black support can be improved to give an improved hydrogenation catalyst for the reduction of aromatic nitro compounds. Such an iron-modified platinum catalyst is particularly useful for the reduction of chloronitro aromatic compounds to the corresponding amines. It has been found that the combination of iron oxide, hydroxide or carbonate with platinum and the method of preparation gives an efficient catalyst.

The platinum and iron are deposited on particles of a nonporous or oleophilic carbon black support as their oxides, hydroxides or carbonates. Such a carbon black support is described in the aforesaid U.S. Pat. No. 2,823,235 and is generally known as an acetylene black or a conductive furnace black. An acetylene black sold commercially is Shawinigan acetylene black. Generally this support will have a surface area, as measured by nitrogen absorption according to known techniques, less than about 300 $m^2/g$, preferably a surface area in the range of about 20–100 $m^2/g$. Particle size and density do not appear to be critical; however, these carbon blacks generally have a density of about 5–12 lbs/$ft^3$ and are very fine in particle size, i.e., 70% by weight are less than 1 micron.

The platinum metal component of the catalyst is present on the carbon black support at a total concentration of about 0.1–10 percent by weight, based on the weight of the carbon black, preferably about 1–5 percent by weight. Iron is present in the form of its carbonate, oxide and/or hydroxide, the molar ratio of iron to platinum being in the range of about 2:1–16:1, preferably in the range of about 4–8:1. It appears that a molar ratio higher than about 8:1 does not add any correspondingly higher benefit in a reduction reaction and a molar ratio lower than about 4:1 gives a drop in catalyst activity, i.e., a longer hydrogenation reaction time. It also appears that as the platinum metal content increases the catalyst becomes less efficient, i.e., at the same nitrobody to platinum ratio the hydrogenation reaction time increases. Thus, there seems to be little advantage in using platinum metal contents over 5 percent.

The catalysts of the present invention are characterized in that they have a greater portion of their metallic component distributed on the substrate surface, thus a greater portion of this metallic component is available for contact with an aromatic nitro compound and hydrogen during a reduction reaction. These catalysts give many advantages over similar catalysts in the reduction reaction and these advantages will be more fully apparent later.

The improved metal distribution on the carbon surface is shown by ESCA (electron spectroscopy for chemical analysis). ESCA measures the intensity ratio of platinum/carbon and iron/carbon and is indicative of the distribution of these metals over the surface area of the carbon support. Higher ESCA values indicate a more favorable metal distribution. It has also been found for the present catalyst that as the total metal content decreases, the ESCA intensity ratio decreases. The use of ESCA spectra in catalyst characterization is described in J. S. Brinen, "Applying Electron Spectroscopy for Chemical Analysis to Industrial Catalysis," *Acc. Chem. Res.*, Vol. 9 (1976), pages 82–92, and in U.S. Pat. No. 4,035,260, issued July 12, 1977, to Schmitt and Brinen, the ESCA disclosures of which are hereby incorporated by reference.

The dispersion of the metals on the catalyst support is characterized by a platinum to carbon ESCA intensity ratio normalized to 1 gram of platinum:

$$\frac{Pt/C}{wt\% \ Pt/100}$$

and a ratio of the iron/carbon ESCA intensity ratio to the platinum/carbon ESCA intensity ratio:

$$\frac{Fe/C}{Pt/C}$$

where Pt/C and Fe/C are ESCA intensities of Pt and Fe, respectively, relative to carbon. The catalysts of the present invention have a normalized platinum to carbon intensity ratio of at least 2.4 and a ratio of the iron/carbon intensity to the platinum/carbon intensity of at least 0.6, preferably 1.0.

Catalysts of the present invention are prepared by using normal catalyst preparation techniques while observing two important conditions—(1) the platinum component of the catalyst is deposited on the surface of the carbon support as its oxide, hydroxide or carbonate (preferably the oxide and/or hydroxide) at a temperature in the range of about 55°–95° C., preferably 90°–95° C.; and (2) prereducing the aforesaid platinum compound to platinum metal at a temperature under about 35° C., preferably at ambient temperature, using any known reducing agent, such as hydrogen, formaldehyde, sodium borohydride and the like, preferably formaldehyde. Typically, the preparation is carried out in an aqueous medium starting with an aqueous slurry of the nonporous carbon particles to which is added, in any order, a water-soluble platinum compound, e.g., chloroplatinic acid, and a water-soluble iron compound, e.g., ferric chloride, ferric nitrate, ferric sulfate, ferric acetate, etc., although the chloride is preferred. For example, both water-soluble compounds can be added to the carbon slurry at the same time at the above-specified temperature and then base added to deposit an oxide, hydroxide or carbonate of platinum and iron. The base used is preferably either an alkali metal hydroxide, carbonate or bicarbonate, although a carbonate such as sodium carbonate is preferred. Upon deposition, both metals are typically present as the oxide, hydroxide or a mixture of both. Alternatively, the water-soluble platinum compound can be added to the carbon slurry at the required temperature and then platinum metal oxide, hydroxide or carbonate deposited by the addition of base as before. This resulting slurry can be cooled and the water-soluble iron compound added at a temperature less than 35° C. and the iron deposited by the addition of base as before.

Preferred procedures, which yield more active catalysts, involve the sequential addition of the water-soluble metal compounds and deposition of the metals by the addition of base at the required temperature. It is preferred that iron be deposited first and then platinum. In all cases, reduction of the oxide, hydroxide or carbonate of platinum to platinum metal is carried out at a temperature below about 35° C. For whatever reason, carrying out the reduction at the platinum deposition temperature results in a catalyst having less metallic component on the carbon surface as shown by ESCA and, thus, a catalyst not as active as a catalyst of the invention. While the catalysts of the invention have a molar ratio of iron to platinum of at least about 2:1, the process of the invention is capable of preparing catalysts having a lower ratio, e.g., as low as 1:1 or lower. A catalyst with such a lower ratio may have lower activity for hydrogenation of chlorobenzenes, but may be an acceptable catalyst for hydrogenations of other nitrobodies.

The catalysts of the present invention are particulary active catalysts for the hydrogenation of aromatic nitro compounds to the corresponding amines. Iron-modified platinum catalysts are especially useful in the hydrogenation of halogen-substituted, preferably chloro-substituted, aromatic nitro compounds to the corresponding halogen-substituted aromatic amines. While these catalysts are particularly advantageous in a batch hydrogenation process since dehalogenation is minimized, reaction time is good, and hydroxylamine accumulation is minimized, a semicontinuous or continuous process can also be carried out. In a continuous process system, the iron-modified platinum catalyst is less sensitive to the presence of water at higher temperatures which promote dehalogenation than similar prior art catalysts.

Aromatic nitro compounds which can be used as starting materials in the hydrogenation process of the present invention have the formula:

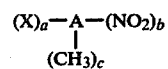

wherein
A is a benzene ring or naphthalene ring, preferably benzene,
X is chloro, fluoro or bromo, preferably chloro,
a is 0 to 2
b is 1 or 2, and
c is 0 or 1.

When a is 0, nonhalogenated nitro compounds are hydrogenated with the subject catalyst with minimal ring reduction. When a is 1 or 2, the iron-modified platinum catalyst is preferred for the hydrogenation of such compounds because of decreased dehalogenation. In all cases, the catalyst enables a continuous hydrogenation to be carried out at higher temperatures, i.e., about 120°–180° C. Of course, lower temperatures can be used, i.e., down to about 80° C. Illustrative aromatic nitro compounds are:

2-chloronitrobenzene
3-chloronitrobenzene
4-chloronitrobenzene
2-bromonitrobenzene
3-bromonitrobenzene
4-bromonitrobenzene
2-chloro-4-nitrotoluene
2-bromo-4-nitrotoluene
4-chloro-2-nitrotoluene
4-bromo-2-nitrotoluene
1-chloro-8-nitronaphthalene 6-chloro-2-nitrotoluene
4-chloro-3-nitrotoluene
2,4-dichloronitrobenzene
2,4-dibromonitrobenzene
3,4-dichloronitrobenzene
3,4-dibromonitrobenzene
3,5-dichloronitrobenzene
2,5-dichloronitrobenzene
2,3-dichloronitrobenzene
nitrobenzene
o-, m- and p-dinitrobenzenes
o-, m- and --nitrotoluenes
dinitrotoluenes
nitronaphthalenes Preferred aromatic compounds are nitrobenzene, o- and p-nitrotoluene, α-nitrophthalene, 1-nitro-3,4-dichlorobenzene, 1-nitro-2-chlorobenzene, 1-nitro-4-chlorobenzene, 1-nitro-2,5-dichlorobenzene and 1-nitro-2,3-dichlorobenzene.

The procedure and conditions needed for the hydrogenation of aromatic nitro compounds are well known in the art. Reference is made to U.S. Pat. Nos. 2,823,235; 3,499,034; 3,145,231 and Applicant's copending application Ser. No. 908,562, filed May 22, 1978. In general, hydrogenation is carried out at a temperature in the range of about 80°–180° C., preferably 120°–150° C. for continuous operation. At temperatures below about 80° C., the reaction rate is too low to make the process economical while temperatures above about 180° C. cause increased dehalogenation in the case of halogen-substituted nitro compounds, may cause ring reduction in the case of unsubstituted nitro compounds and may cause undesirable decomposition of the nitro compound and its resulting amine.

The hydrogenation pressure is usually in the range of about 790–7000 kPa (about 100–1000 psig) by charging hydrogen at these pressures. The preferred hydrogen pressure is in the range of about 790–4240 kPa (about 100–600 psig), more preferably in the range of about 790–3550 kPa (about 100–500 psig). With a hydrogen pressure less than about 100 psig, the reaction rate is reduced while pressures above about 1000 psig provide mechanical difficulties which may exceed the advantages obtained by the increased pressure.

It is advantageous to have a cycloaliphatic nitrogen base, such as morpholine and others described in U.S. Pat. No. 3,145,231, present in the hydrogenation reaction medium in an amount corresponding to a mole ratio of the cycloaliphatic base to halogen-substituted nitro compound of about 0.01–1.5. A cycloaliphatic nitrogen base not only aids in suppressing dehalogenation but also inhibits corrosion by preventing development of acidity during hydrogenation of the halogen-substituted aromatic nitro compound. If desired, the cycloaliphatic base can be removed from the amine product by washing with water. Other dehalogenation inhibitors known in the art can be used.

The invention can be further understood by the following Procedures and Examples in which parts and percentages are by weight unless otherwise indicated.

In the Examples that follow, the following exemplary procedures were used to prepare catalyst:

Procedure A

One liter of deionized water, 35.8 g of ferric chloride hexahydrate (0.132 mole, 7.4 g Fe), and 62.5 g Shawinigan Black[1] were added to a 3-liter, round bottom flask equipped with an agitator. The resulting slurry was heated to 90° C., and a solution of 21.3 g of sodium carbonate (0.201 mole) in 210 ml of deionized water was added over a period of 1 hour at 90° C. and agitated for an additional 1 hour at the same temperature. An aqueous solution (31.6 ml) of 10% chloroplatinic acid (3.16 g Pt, 0.016 mole Pt) was added dropwise over a period of 15 minutes at 90° C.

[1] Shawinigan Black (Acetylene Black 100) having a surface area of 35 sq. meters/g, a particle size of 70% less than 1 micron and a density of 10 lbs/ft$^3$. Enough sodium carbonate from a solution of 23.2 g sodium carbonate in 210 ml of deionized water was added over a period of 0.5 hour to give a positive test for brilliant yellow pH paper (paper turns orange at 50–60 ml). The slurry was agitated for an additional hour at 90° C. while maintaining a positive test with the pH paper. After cooling to 25° C., a 500 ml portion of the slurry was filtered, washed with 3×150 ml deionized water and the resulting unreduced wet catalyst bottled for later reduction. To the remaining slurry was added the remainder of the above sodium carbonate solution over a period of 0.5 hour at 25° C. Then, a solution of 16 ml of 37% formaldehyde dissolved in 100 ml of water was added over a period of 0.5 hour at 25° C. Agitation was continued for 1 additional hour at the same temperature. The resulting prereduced catalyst was filtered, washed with 3×300 ml deionized water and stored in a capped bottle.

This particular catalyst has a bulk Pt content of 4% (5% based on carbon) and an Fe/Pt molar ratio of 8/1. This procedure was used to prepare other catalysts having different Pt contents and/or Fe/Pt ratios, different precipitation and reduction temperatures. Catalysts showing temperature effects are set forth in Table I while catalysts having different compositions are set forth in Table II.

Procedure B

One liter of deionized water and 62.5 g of Shawinigan Black were added to a 3-liter, round bottom flask equipped with an agitator and the resulting slurry heated to 90° C. An aqueous solution (31.6 ml) of 10% chloroplatinic acid (3.16 g Pt, 0.016 mole Pt) was added all at once after which enough sodium carbonate from a solution of 23.2 g of sodium carbonate in 210 ml of deionized water was added over a period of 15 minutes at 90° C. to give a positive test for brilliant yellow pH paper (paper turns orange after 50–60 ml). Agitation was continued for an additional 15 minutes at the same temperature while maintaining a positive test with the pH paper. After cooling to 25° C., 35.8 g of ferric chloride hexahydrate (7.4 g Fe, 0.132 mole Fe) was added over a period of 10 minutes. A solution of 21.3 g of sodium carbonate (0.201 mole) in 210 ml of deionized water was added over a period of 1 hour at 25° C. and agitated for an additional 1 hour at the same temperature. A 500 ml portion of the slurry was filtered, washed with 3×150 ml deionized water and the resulting unreduced catalyst bottled. To the remaining slurry was added the remainder of the above sodium carbonate solution over a period of 0.5 hour at 25° C. A solution of 16 ml of 37% formaldehyde dissolved in 100 ml of water was then added over a period of 0.5 hour at 25° C. Agitation was continued for an additional 1 hour at the same temperature. The resulting prereduced catalyst was filtered, washed with 3×500 ml of deionized water and the wet catalyst cake bottled.

This particular catalyst has a bulk Pt content of 4% (5% based on C) and an Fe/Pt molar ratio of 8/1. This procedure is used to prepare other catalysts having different Pt contents and/or Fe/Pt ratios and different precipitation and reduction temperatures. Catalysts showing temperature effects are set forth in Table I while catalysts having different compositions are set forth in Table II.

In the Examples, both unreduced and reduced catalyst samples were analyzed by ESCA using a Du Pont model 650B Electron Spectrometer system with a multichannel signal analyzer.

An indication of catalyst activity in the Examples is its ability to give decreased reaction times in the catalytic hydrogenation of aromatic nitro compounds to their corresponding amines. Hydrogenations for Examples 1–18 in Tables I–III were carried out batchwise to prepare 3,4-dichloroaniline from 1-nitro-3,4-dichlorobenzene as follows:

To a standard 1-liter Parr titanium autoclave equipped with a cooling coil, thermocouple, pressure gauge, and an agitator were charged 768 g of 1-nitro-3,4-dichlorobenzene, 8 ml of morpholine and enough catalyst to give a nitrobody to Pt weight ratio of 70,000. The air in the autoclave was purged with nitrogen, and then the nitrogen replaced with hydrogen. After heating to 85° C. at a slight hydrogen pressure and no agitation, the hydrogen pressure was increased to 300 psig and agitation begun at 1000 revolutions per minute. The temperature was allowed to rise to 95° C. and was controlled at that temperature with cooling water. The hydrogen pressure was maintained at 300 psig by using a reserve hydrogen cylinder kept above 600 psig and equipped with a pressure regulator. Data on autoclave temperature and pressure, and pressure in the reserve hydrogen cylinder was recorded graphically. Readings on autoclave temperature and pressure, and reserve hydrogen cylinder pressure and pressure drop were taken every ten minutes or less. When the reaction was completed, as indicated by cessation of hydrogen uptake and heat of reaction, the autoclave was cooled to 80° C., hydrogen displaced with nitrogen and the products removed. The time of reaction (cessation in hydrogen uptake) was noted.

The various catalysts prepared by the above procedures showing temperature effects in preparation and showing the effects of varying the Fe/Pt molar ratio are set forth in Tables I and II. Procedures A and B recited in Table II are as given above, i.e., the same procedure conditions as for Examples 1 and 3.

TABLE I

The Effect of Temperature in the Preparation of Iron-Activated Platinum Catalyst on an Oleophilic Carbon Black

| Example No. | Procedure | Temperature (°C.) | | |
|---|---|---|---|---|
| | | Fe ppt | Pt ppt | Formaldehyde Reduction |
| 1 | A | 90 | 90 | 25 |
| Control A | A | 90 | 90 | 90 |
| Control B | A | 90 | 90 | 90[a] |
| 2 | A | 55 | 55 | 25 |
| Control C | A | 25 | 25 | 25 |
| 3 | B | 25 | 90 | 25 |
| 4 | B | 90 | 90[b] | 25 |
| 5 | B | 25 | 90[b] | 25 |

| | | ESCA Intensity Ratio | | | | | Hydrogenation |
|---|---|---|---|---|---|---|---|
| Ex. No. | Unreduced | | Reduced | | | | Time (Min.) |
| | Pt/C | Fe/C | Pt/C | Fe/C | Pt/C / Pt | Fe/C / Pt/C | |
| 1 | .18 | .060 | 0.12 | .12 | 3.0 | 1.0 | 84 |
| Control A | .16 | .037 | .079 | .042 | 2.0 | 0.53 | 150 |
| Control B | .16 | .037 | .13 | .062 | 3.1 | 0.48 | 106 |
| 2 | .10 | .36 | .096 | .17 | 2.4 | 1.8 | 89 |
| Control C | .026[c] | .31 | — | — | — | — | — |
| 3 | .15 | .46 | .11 | .13 | 2.8 | 1.2 | 77 |
| 4 | .14 | .14 | .11 | .14 | 2.8 | 1.3 | 100 |
| 5 | .14 | .52 | .10 | .14 | 2.5 | 1.4 | 72 |

[a] Cooled rapidly to 25° C. 5 minutes after the addition of formaldehyde—about 10 minutes at temperature.
[b] Increased agitation time from 15 min. to 1 hour after addition of sodium carbonate solution to chloroplatinic acid.
[c] Incomplete precipitation of ionic platinum, not run.

TABLE II

The Effect of Iron to Platinum Molar Ratio in the Preparation of Iron-Activated Platinum Catalyst on an Oleophilic Carbon Black

| Example No. | Procedure | Mole Ratio Fe/Pt | ESCA Intensity Ratio | | | | | Hydrogenation Time (Min.) |
|---|---|---|---|---|---|---|---|---|
| | | | Unreduced | | Reduced | | | |
| | | | Pt/C | Fe/C | Pt/C | Fe/C | Pt/C / Pt | Fe/C / Pt/C | |
| 6 | A | 8 | .21 | .088 | .13 | .15 | 3.3 | 1.2 | 65 |
| 7 | A | 4 | .19 | .031 | .12 | .12 | 3.0 | 1.0 | 70 |
| 8 | A | 1 | .18 | .022 | .13 | .035 | 3.3 | .27 | 85 |
| 9 (Ex. 3) | B | 8 | .15 | .46 | .11 | .13 | 2.8 | 1.2 | 77 |
| 10 | B | 4 | .17 | .24 | .098 | .11 | 2.5 | 1.1 | 76 |
| 11 | B | 16 | .12 | .64 | .092 | .18 | 2.3 | 2.0 | 79 |

In the above Tables, Example 1 shows that the described procedure gives a more active catalyst than when the prereduction is carried out at 90° C. (Control A). Decreasing the prereduction time at 90° C. from 1.5 hours to 10 minutes increased catalyst activity, but the rapid cooling necessary is impractical on a commercial scale (Control B). The catalysts of the invention have the higher portion of the bulk platinum and iron distributed on the surface as indicated by the Pt/C and Fe/C ESCA intensity ratios.

In Example 2, even though the platinum dispersion is marginal $$\left(\frac{Pt/C}{Pt} \text{ of } 2.4\right),$$

the combination of marginal Pt and good iron surface dispersion $$\left(\frac{Fe/C}{Pt/C} \text{ of } 1.8\right)$$

gives an active catalyst compared with comparison Example 1. When the is low as in Example 8, a less active catalyst is produced even with the better platinum surface dispersion $$(\frac{Pt/C}{Pt} \text{ of } 3.3)$$

compared with its companion example, Example 6. The use of a low iron to platinum molar ratio, even with the preferred process, gives a low iron/carbon ESCA and is not a preferred hydrogenation catalyst.

EXAMPLES 12–14

Procedure A was followed to the separation of unreduced catalyst, and then three alternative reductions of the same batch of unreduced catalyst were carried out. Example 12 was a reduction with formaldehyde as given. Example 13 was a reduction with hydrogen carried out as follows:

Ten grams of the unreduced catalyst along with 500 ml deionized water were charged to an autoclave equipped with a thermocouple, pressure gauge and agitator. Air in the autoclave and lines was displaced by pressurizing with nitrogen and releasing the pressure through a vent system. The nitrogen was then displaced by nitrogen by 5 successive pressurizings to 300 psig and venting to zero. The catalyst slurry was agitated for 2 hours at 25° C. at a hydrogen pressure of 300 psig. After the autoclave and lines were purged, the hydrogen-reduced catalyst was filtered, washed with deionized water and the resulting wet cake placed in a capped bottle.

Example 14 was a reduction with sodium borohydride carried out as follows:

Ten grams of the unreduced catalyst was slurried in 100 ml of distilled water under a blanket of nitrogen. A solution of 0.5 g of sodium borohydride in water was added dropwise over 5 minutes. Evolution of hydrogen gas occurred immediately. The slurry was stirred for an additional 1 hour, and the resulting prereduced catalyst was filtered, washed and bottled as before.

The results of the ESCA analysis and hydrogenation are shown in Table III.

EXAMPLE 15

Procedure A was repeated except the amount of iron and platinum was reduced to give a bulk platinum content of 1.3% while maintaining an Fe/Pt molar ratio of 8/1, i.e., for every 1 g of Shawinigan Black there was used 0.16 g ferric chloride hexahydrate, 0.014 g of platinum from chloroplatinic acid, 0.07 ml of 37% formaldehyde, and corresponding amounts of sodium carbonate, all dissolved in the stated amounts of deionized water.

The results of the ESCA analysis and hydrogenation are shown in Table III.

EXAMPLE 16

Unreduced catalyst from Example 15 was reduced with hydrogen using the procedure of Example 12.

The results of the ESCA analysis and hydrogenation are shown in Table III.

EXAMPLE 17

Procedure A was repeated except the amount of iron and platinum was increased to give a bulk platinum content of 9.6% and an Fe/Pt molar ratio of 4/1. For every 1 g of Shawinigan Black there was used 0.57 g of ferric chloride hexahydrate, 0.13 g platinum from chloroplatinic acid, 0.26 ml 37% formaldehyde, and corresponding amounts of sodium carbonate, all dissolved in the stated amounts of deionized water.

The results of the ESCA analysis and hydrogenation are shown in Table III.

EXAMPLE 18

Unreduced catalyst from Example 17 was reduced with hydrogen using the general procedure of Example 13. In the hydrogen reduction, 10 g of unreduced catalyst in 200 ml distilled water was placed in the autoclave. The system was purged of air by nitrogen and hydrogen as described. Hydrogen was passed through the slurry for two hours at 25° C.

The results of the ESCA analysis and hydrogenation are shown in Table III.

TABLE III

The Effect of Reducing Agent in the Preparation of Iron-Activated Platinum Catalyst on an Oleophilic Carbon Black

| Example No. | Reducing Agent | Pt % | Unreduced Pt/C | Unreduced Fe/C | ESCA Intensity Ratio Reduced Pt/C | ESCA Intensity Ratio Reduced Fe/C | Reduced Pt/C / Pt | Reduced Fe/C / Pt/C | Hydrogenation Time (Min.) |
|---|---|---|---|---|---|---|---|---|---|
| 12 | $H_2CO$ | 4 | .16 | .037 | .12 | .10 | 3.0 | .83 | 100 |
| 13 | $H_2$ | 4 | .16 | .037 | .10 | .070 | 2.5 | .70 | 103 |
| 14 | $NaBH_4$ | 4 | .16 | .037 | .076 | .076 | 1.9 | 1.0 | 110 |
| 15 | $H_2CO$ | 1.3 | .057 | .029 | .049 | .033 | 3.8 | .67 | 90 |
| 16 | $H_2$ | 1.3 | .057 | .029 | .036 | .050 | 2.8 | 1.4 | 88 |
| Control E | — | 9.6 | .49 | .05 | — | — | — | — | 150 |
| 17 | $H_2CO$ | 9.6 | .49 | .05 | .33 | .12 | 3.4 | .36[a] | 103 |
| 18 | $H_2$ | 9.6 | .49 | .05 | .28 | .11 | 2.9 | .39[a] | 90 |

[a]A low value due to a decrease in the moles of iron relative to platinum from 8:1 to 4:1.

As can be seen in Table III, catalysts prepared using formaldehyde as the reducing agent generally have a higher proportion of the metallic components on the surface than catalysts prepared using other reducing agents, although these latter catalysts have a higher proportion than Controls A or C.

EXAMPLE 19

Using the hydrogenation procedure described previously for Examples 1–18, 4-nitrochlorobenzene was hydrogenated using a catalyst prepared as in Example 1. The hydrogenation time for this catalyst was 65 minutes compared to a time of 140 minutes for a control catalyst prepared as in Control A.

EXAMPLE 20

Using the same catalysts as prepared in Example 19, nitrobenzene was hydrogenated by the procedure described previously for Examples 1–18. The reduction time for the catalyst prepared as in Example 1 was 78 minutes compared to a reduction time of 118 minutes for the catalyst prepared as in Control A.

EXAMPLES 21 and 22

Example 21 was a batch hydrogenation of 1-nitro-3,4-dichlorobenzene and Example 22 was a batch hydrogenation of o-nitrochlorobenzene. The catalyst used in both examples was prepared as in Example 1. The two hydrogenations provided means for taking samples during the hydrogenations for analyses of tar formation, dechlorination and chlorophenylhydroxylamine (CPHA) buildup.

The hydrogenations were carried out as follows:

To a one-liter titanium autoclave equipped with a cooling coil, thermocouple, pressure gauge and an agitator were charged 768 g of nitrobody, enough catalyst to give a nitrobody to Pt weight ratio of 100,000 and 1 percent morpholine based on nitrobody. The air in the autoclave was purged with nitrogen and then the nitrogen replaced with hydrogen. After heating to 80° C. at 10 psig hydrogen pressure and no agitation, the hydrogen pressure was increased to 100 psig and agitation begun at 1000 revolutions per minute. The temperature was kept at 80° C. for Example 22 with cooling water regulated with an automatic valve, and the temperature was allowed to rise to 95° C. for Example 21 before cooling water was circulated to maintain temperature. The hydrogen pressure was then increased to 200 psig and than 500 psig as required to maintain a steady hydrogen consumption, and, therefore, controlled heat of reaction. Hydrogen pressure was controlled by using a 4-liter reserve hydrogen cylinder kept above 600 psig and equipped with a pressure regulator. The amount of hydrogen consumed was monitored by following the decrease in reservoir pressure. The time of reaction (hydrogen uptake ceases) was noted. In each Example, two approximately 20 g samples were taken (the first to purge the sample line) at one hour intervals through a sintered metal catalyst filter into glass sample vials. Each sample was analyzed for weight percent chlorophenylhydroxylamine (CPHA) by infrared with a Cary 14 Spectrophotometer, weight percent p-chloroaniline (PCA) and/or aniline (An) by gas chromatography with a Perkin-Elmer 900 Gas Chromatograph and weight percent residual tars by evaporating the sample at 95° C. and 1 millimeter pressure. The pH of the water layer was also measured.

The results of the analysis are in Table IV.

TABLE IV

| Example No. | Red. Time (Min.) | CPHA (wt %) 35$^a$ | 50$^a$ | 60$^a$ | Product (wt %) PCA | An | Tar | Water Layer pH |
|---|---|---|---|---|---|---|---|---|
| 21 | 235 | 2.7 | 2.8 | 2.3 | nil | nil | 1.4 | 9.4 |
| 22 | 210 | 6.4 | 5.5 | 4.0 | — | 0.1 | 2.3 | 7.7 |

$^a$H$_2$ consumption, percent of theory.

The results in Table IV show that the use of an iron-modified platinum catalyst optimizes four factors important to the hydrogenation of chlorinated benzenes: (1) fast rate, (2) low tars, (3) low dehalogenation, and (4) maintaining a low hydroxylamine concentration.

EXAMPLE 23

Hydrogenations of 1-nitro-3,4-dichlorobenzene were carried out as described for Examples 1–18 using catalysts prepared as in Example 1. The only difference in catalyst preparation was the carbon black supports used. The results are shown in Table V.

TABLE V

Effect of Support on Reduction Time

| Example No. | Support | Surface Area (m$^2$/g) | Particle Size | Red. Time (Min.) |
|---|---|---|---|---|
| 23 | Shawinigan Black | 35 | 70% <1 micron | 84 |
| Control F | Darco G-60 | 500 | 70% <30 microns | 133 |
| Control G | Carbon Black | 1050 | 70% >10 microns | 130$^a$ |

$^a$Hydrogenation incomplete when stopped; reaction mixture went acid during the run.

EXAMPLES 24–26

These examples show continuous hydrogenations of 1-nitronaphthalene (Example 24), 2-nitrotoluene (Example 25) and 4-nitrotoluene (Example 26) using a catalyst prepared as in Example 1.

The hydrogenations were carried out as follows:

The continuous hydrogenation was conducted in a reaction system comprising a one-gallon baffled autoclave equipped with an agitator, gas sparger, heater and cooling coils; a 1.5 gallon flasher equipped with an external heating coil; and an internal filter (thickener).

The autoclave was charged with 2400 cc of amine corresponding to the nitrobody to be reduced. Catalyst (0.5%) was also charged into the autoclave. The flasher was also charged with 2500 cc of a heel of the same composition as that in the autoclave. After replacing the atmosphere in the total system with hydrogen by first pressurizing with nitrogen and venting, followed by pressurizing and venting with hydrogen, the autoclave was brought to 130°–140° C. and 1550–2170 kPa (210–300 psig) hydrogen pressure. The heel in the autoclave was continuously pumped through a reducing valve at a rate of about 100 pounds per hour to the flasher and pumped back to the autoclave. The flasher operated at atmospheric pressure and was kept at 110°–120° C. by external heating, when required. Nitrobody was fed to the autoclave at a feed rate of 1–2 pounds per hour. Water was continuously distilled out of the flasher in sufficient quantity to insure a single organic phase in the system. Under steady state conditions, the heat of reaction was removed by means of the cooling coil in the autoclave and by the distillation of water in the flasher so as to maintain the reaction temperature of 130°–140° C. Hydrogen pressure was maintained at 1550–2170 kPa (210–300 psig). The liquid levels in the autoclave and the flasher were maintained at essentially the original levels by removing the product through the internal filter (thickener) at a rate corresponding to the nitrobody fed to the autoclave. Thus, from 1–2% of the recirculating liquid reaction medium was removed via the internal filter, the remainder of the medium, together with the catalyst, being returned to the autoclave. The results are shown in Table VI.

TABLE VI

| Example No. | Productivity lb. hr.-gal. | Tar (wt %) | % Ring Reduction |
|---|---|---|---|
| 26 | 1.6 | 0.5–1.0 | <0.1 |
| 27 | >2.8 | 0.2 | 0.03 |
| 28 | >2.8 | 0.25 | 0.03 |

The results in Table VI show that the use of an iron-modified platinum catalyst is useful in hydrogenating nonhalogenated aromatic compounds, giving high productivity while keeping tars and ring reduction low.

I claim:

1. A hydrogenation catalyst consisting essentially of an oleophilic carbon black support having a surface area of 20–100 m$^2$/g, said support having on its surface about 1–5 percent by weight of the support of platinum metal and iron in the form of its oxide or hydroxide, the molar ratio of iron to platinum being in the range of about 4–8:1, said catalyst having:
  (1) a ratio of platinum/carbon ESCA intensity ratio to the total platinum content, expressed by its weight percent concentration/100, of at least about 2.4; and
  (2) a ratio of the iron/carbon ESCA intensity ratio to the platinum/carbon ESCA intensity ratio of at least about 1.0.

2. A process for improving the distribution of metallic component in the preparation of a hydrogenation catalyst having a carbon black support comprising: (a) depositing onto oleophilic carbon black particles having a surface area less than about 300 m$^2$/g, at a temperature in the range of about 55°–95° C., an oxide, hydroxide or carbonate of platinum, the concentration of the platinum being in the range of about 0.1–10 percent by weight based on the weight of the carbon black; (b) depositing an oxide, hydroxide or carbonate of iron onto the carbon black particles in an amount to provide a molar ratio of iron to platinum in the range of about 1:1–16:1, and (c) reducing the platinum oxide, hydroxide or carbonate to platinum metal at a temperature less than about 35° C.

3. The process of claim 2 conducted in an aqueous medium and reducing is conducted with a reducing agent selected from the group consisting of hydrogen, formaldehyde and sodium borohydride.

4. The process of claim 2 or claim 3 wherein the molar ratio of iron to platinum is in the range of about 2:1–16:1.

5. The process of claim 2 or claim 3 wherein the molar ratio of iron to platinum is in the range of about 4–8:1, the concentration of platinum is about 1–5 percent and the surface area of the carbon black is in the range of about 20–100 m$^2$/g.

6. A process for improving the distribution of metallic component in preparing a hydrogenation catalyst comprising: (a) mixing in an aqueous medium at a temperature in the range of about 90°–95° C. a water-soluble, platinum compound, carbon black particles having a surface area less than about 300 m$^2$/g and a water soluble iron compound, said platinum compound present in an amount sufficient to give about 0.1–10 percent by weight platinum, based on the weight of the carbon black, and the iron compound present in an amount sufficient to give an iron to platinum molar ratio in the range of about 2:1–16:1; (b) adding a base in an amount sufficient to deposit on the carbon black an oxide or hydroxide of iron and platinum; (c) adding formaldehyde to the aqueous mixture, at a temperature less than about 35° C., in an amount sufficient to reduce essentially all of the platinum oxide or hydroxide to elemental platinum; and (d) recovering the catalyst from the aqueous mixture.

7. The process of claim 6 wherein steps (a) and (b) are carried out as follows: ferric chloride is added to an aqueous slurry of the carbon black particles; precipitating at least one of an oxide or hydroxide of iron onto the carbon black particles by adding to the slurry an alkali metal carbonate; adding the water-soluble platinum compound to the slurry and then adding an alkali metal carbonate to precipitate at least one of an oxide or hydroxide of platinum onto the carbon black particles.

8. The process of claim 6 wherein steps (a) and (b) are carried out as follows: adding the water-soluble platinum compound to an aqueous slurry of the carbon black particles; precipitating at least one of an oxide or hydroxide of platinum onto the carbon black particles by adding to the slurry an alkali metal carbonate; adding ferric chloride to the slurry and then adding an alkali metal carbonate to precipitate at least one of an oxide or hydroxide of iron onto the carbon black particles.

9. The process of claim 8 wherein the slurry is cooled to below about 35° C. prior to the addition of the ferric chloride.

10. The process of claim 7 or claim 8 wherein the platinum compound is chloroplatinic acid, the carbon black has a surface area in the range of about 20–100 m$^2$/g, the alkali metal carbonate is sodium carbonate, and the molar ratio of iron to platinum is in the range of about 4–8:1.

11. In a process for preparing an aromatic amine by hydrogenating the corresponding nitro compound in the presence of a noble metal catalyst the improvement comprising: hydrogenating the nitro aromatic compound in the presence of the catalyst of claim 1.

12. The process of claim 11 wherein the nitro compound has the formula

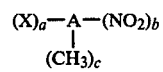

wherein
  A is a benzene ring or a naphthalene ring,
  X is chloro, fluoro or bromo,
  a is 0 to 2,
  b is 1 or 2, and
  c is 0 or 1.

13. The process of claim 12 wherein a is 0.

14. The process of claim 12 wherein a is 1 or 2 and X is chloro.

15. The process of claim 14 wherein the catalyst is the catalyst of claim 3.

16. The process of claim 15 wherein the nitro compound is at least one of 1-nitro-3,4-dichlorobenzene, 1-nitro-2-chlorobenzene, 1-nitro-4-chlorobenzene, 1-nitro-2,5-dichlorobenzene and 1-nitro-2,3-dichlorobenzene.

17. The process of claim 13 wherein the nitro compound is α-nitronaphthalene, o-nitrotoluene, p-nitrotoluene or nitrobenzene.

* * * * *